United States Patent
Morita

(10) Patent No.: US 11,793,494 B2
(45) Date of Patent: Oct. 24, 2023

(54) ULTRASOUND PROBE, ULTRASOUND DIAGNOSTIC APPARATUS, AND METHOD FOR PRODUCING BACKING MATERIAL

(71) Applicant: Konica Minolta, Inc., Tokyo (JP)

(72) Inventor: Kiyokazu Morita, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 619 days.

(21) Appl. No.: 16/793,417

(22) Filed: Feb. 18, 2020

(65) Prior Publication Data

US 2020/0268358 A1    Aug. 27, 2020

(30) Foreign Application Priority Data

Feb. 26, 2019 (JP) ................. 2019-032580

(51) Int. Cl.
| | | |
|---|---|---|
| *A61B 8/00* | (2006.01) | |
| *B29C 43/00* | (2006.01) | |
| *B29L 31/40* | (2006.01) | |
| *B29K 507/04* | (2006.01) | |
| *B29K 63/00* | (2006.01) | |

(Continued)

(52) U.S. Cl.
CPC ............ *A61B 8/546* (2013.01); *A61B 8/4444* (2013.01); *B29C 43/003* (2013.01); *B29C 43/56* (2013.01); *B29C 2043/561* (2013.01); *B29K 2063/00* (2013.01); *B29K 2507/04* (2013.01); *B29K 2509/04* (2013.01); *B29K 2995/0013* (2013.01); *B29L 2031/40* (2013.01)

(58) Field of Classification Search
CPC ..... A61B 8/546; A61B 8/4444; B29C 43/003; B29C 43/56; B29C 2043/561; B29K 2063/00; B29K 2507/04; B29K 2509/04; B29K 2995/0013; B29L 2031/40
See application file for complete search history.

(56) References Cited

U.S. PATENT DOCUMENTS

| | | | | |
|---|---|---|---|---|
| 2005/0275313 | A1* | 12/2005 | Yamashita | ............ B06B 1/0622 310/327 |
| 2006/0043839 | A1* | 3/2006 | Wildes | ................. G10K 11/004 310/327 |

(Continued)

FOREIGN PATENT DOCUMENTS

| | | | |
|---|---|---|---|
| JP | 2005-347804 A | 12/2005 | |
| JP | 2006-033801 A | 2/2006 | |

(Continued)

OTHER PUBLICATIONS

Machine translation of JP2014208727A (Year: 2014).*

(Continued)

*Primary Examiner* — John Denny Li
(74) *Attorney, Agent, or Firm* — LUCAS & MERCANTI, LLP

(57) ABSTRACT

An ultrasound probe of the present invention has a piezoelectric element and a backing material disposed on one direction side with respect to the piezoelectric element, the backing material containing heat conductive particles. The backing material has a heat conductivity of 2.0 W/mk or more, and the content of the heat conductive particles is less than 30 vol % based on the total volume of the backing material.

12 Claims, 3 Drawing Sheets

(51) Int. Cl.
   *B29C 43/56*   (2006.01)
   *B29K 509/04*   (2006.01)

(56) References Cited

U.S. PATENT DOCUMENTS

| | | | | |
|---|---|---|---|---|
| 2007/0016064 | A1* | 1/2007 | Yamashita | G10K 11/002 600/459 |
| 2008/0098816 | A1* | 5/2008 | Yamashita | B06B 1/0629 310/335 |
| 2015/0173712 | A1* | 6/2015 | Song | A61B 8/4483 29/25.35 |

FOREIGN PATENT DOCUMENTS

| JP | 2006-325954 A | 12/2006 | | |
|---|---|---|---|---|
| JP | 2008-118212 A | 5/2008 | | |
| JP | 2009-060501 A | 3/2009 | | |
| JP | 2009-261840 A | 11/2009 | | |
| JP | 2012-000219 A | 1/2012 | | |
| JP | 2012000219 A | * | 1/2012 | |
| JP | 2014208727 A | * | 11/2014 | C01B 31/02 |
| JP | 2017-527375 A | | 9/2017 | |

OTHER PUBLICATIONS

Machine translation of JP2012000219A (Year: 2012).*
Khosla A et al., Carbon fiber doped thermosetting elastomer for flexible sensors: physical properties and microfabrication. Sci Rep. Aug. 17, 2018;8(1):12313. doi: 10.1038/s41598-018-30846-3 (Year: 2018).*
https://www.makeitfrom.com/material-properties/Ethylene-Vinyl-Acetate-EVA (Year: 2023).*
JPO, Notice of the Reasons for Rejection for the corresponding Japanese Patent Application No. 2019-032580, dated Jun. 28, 2022, with English translation.
Decision of Dismissal of Amendment dated Jan. 24, 2023 for the corresponding Japanese Patent Application No. 2019-032580 (with machine translation, 9 pages).
Notice of the Reasons for Rejection for the corresponding Japanese Patent Application No. 2019-032580, dated Oct. 25, 2022, with English translation.

* cited by examiner

ULTRASOUND PROBE, ULTRASOUND DIAGNOSTIC APPARATUS, AND METHOD FOR PRODUCING BACKING MATERIAL

CROSS REFERENCE TO RELATED APPLICATIONS

The entire disclosure of Japanese Patent Application No. 2019-032580 filed on Feb. 26, 2019, is incorporated herein by reference in its entirety.

BACKGROUND

Technological Field

The present invention relates to an ultrasound probe, an ultrasound diagnostic apparatus, and a method for producing a backing material.

Description of Related Art

An ultrasound diagnostic apparatus enables a shape, movement, and the like of tissues to be obtained as ultrasound diagnostic images with a simple operation that an ultrasound probe, which is connected to the ultrasound diagnostic apparatus or is configured to be communicable with the ultrasound diagnostic apparatus, is brought into contact with a body surface of a subject including a human, other animals, and the like or is inserted into the body. The ultrasound diagnostic apparatus has an advantage of being capable of performing inspection repeatedly because of its high safety.

The ultrasound probe incorporates a piezoelectric element and the like transmitting and receiving ultrasound. The piezoelectric element receives an electric signal (transmission signal) from the ultrasound diagnostic apparatus, converts the received transmission signal into an ultrasound signal, transmits the ultrasound signal, receives ultrasound reflected in the living body, converts the ultrasound into an electric signal (reception signal), and transmits the reception signal converted into the electric signal to the ultrasound diagnostic apparatus.

The ultrasound probe has a backing material on the side opposite to the surface of the piezoelectric element faced to a subject (hereinafter, regarding a member constituting the ultrasound probe, a surface facing an ultrasound irradiation direction (a surface faced to the subject) is also referred to as the "front surface," and a surface facing a direction on the side opposite to the ultrasound irradiation direction (a surface on the side opposite to the surface faced to the subject) is also referred to as the "rear surface"). The backing material attenuates (including, absorbs and scatters) ultrasound transmitted from the piezoelectric element to the rear surface side and suppresses occurrence of a noise (artifact) caused by the ultrasound transmitted to the rear surface side being reflected from an end face of the backing material. The backing material radiates heat from the piezoelectric element to the rear surface side and suppresses overheat or the like of an acoustic lens in contact with the subject, which is caused by heat generated in the piezoelectric element.

For this reason, various backing materials having an enhanced heat conductivity have been contemplated.

For example, Japanese Patent Application Laid-Open No. 2006-325954 discloses an ultrasound probe having a piezoelectric transducer constituted by a single crystal material of a perovskite structure, and an acrostic backing material formed in the lower part of the piezoelectric transducer described above, the backing material including an ethylene-vinyl acetate rubber including a carbon fiber having a diameter of 20 µm or less, and a carbon fiber having a diameter of 20 µm or less. The backing material described above, which has an excellent heat radiation property, can make temperature characteristics of the sensitivity of the ultrasound probe good, and thus, is supposed to be able to improve the image quality of tomographic images from an ultrasound diagnostic apparatus.

Japanese Unexamined Patent Application Publication No. 2017-527375 discloses an ultrasound probe having a transducer assembly operable to propagate ultrasound energy, and a cooling system including one or more graphene layers, the cooling system being disposed so as to transfer heat generated by the transducer assembly described above. Containing the graphene described above, the ultrasound probe is supposed to be able to not only have a good heat conductivity but also have an extremely low acoustic impedance.

However, in order to enhance the heat conductivity of the backing material by means of the carbon fiber described in Patent Literature 1, it is necessary to use a carbon fiber having a length of at least 3 mm, and this large carbon fiber may degrade the image quality in some cases.

According to the findings of the present inventors, in an attempt to enhance the heat conductivity of the backing material by means of the graphene described in Patent Literature 2, it was necessary to add a large amount of graphene to the backing material. When a large amount of graphene is contained in the backing material, there has been a problem in that ultrasound transmitted to the rear surface side is not sufficiently attenuated.

SUMMARY

The present invention has been made in the view of the above problem, and an object of the present invention is to provide an ultrasound probe having a backing material having high heat conduction and good acoustic characteristics, an ultrasound diagnostic apparatus having the backing material described above, and a method for producing the backing material described above.

The present invention has been made based on a concept in which the heat conduction of a backing material is enhanced by allowing the backing material to contain heat conductive particles. In this case, the orientation state of the heat conductive particles in the backing material is adjusted.

To achieve at least one of the abovementioned objects, according to an aspect of the present invention, an ultrasound probe reflecting one aspect of the present invention comprises: a piezoelectric element; and a backing material disposed on one direction side with respect to the piezoelectric element, the backing material containing heat conductive particles, wherein the backing material has a heat conductivity of 2.0 W/mk or more, and a content of the heat conductive particles is less than 30 vol % based on a total volume of the backing material.

To achieve at least one of the abovementioned objects, according to another aspect of the present invention, an ultrasound diagnostic apparatus reflecting one aspect of the present invention comprises the ultrasound probe described above.

To achieve at least one of the abovementioned objects, according to another aspect of the present invention, a method for producing a backing material for an ultrasound probe, reflecting one aspect of the present invention comprises: mixing a matrix resin and a heat conductive resin to prepare a mixture, and molding the mixture, wherein the mixture contains less than 30 vol % of the heat conductive particles based on a total volume of the mixture, and the mixture has a heat conductivity of 2.0 W/mk or more.

BRIEF DESCRIPTION OF DRAWINGS

The advantageous and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

1. Ultrasound Probe

Figure 1:
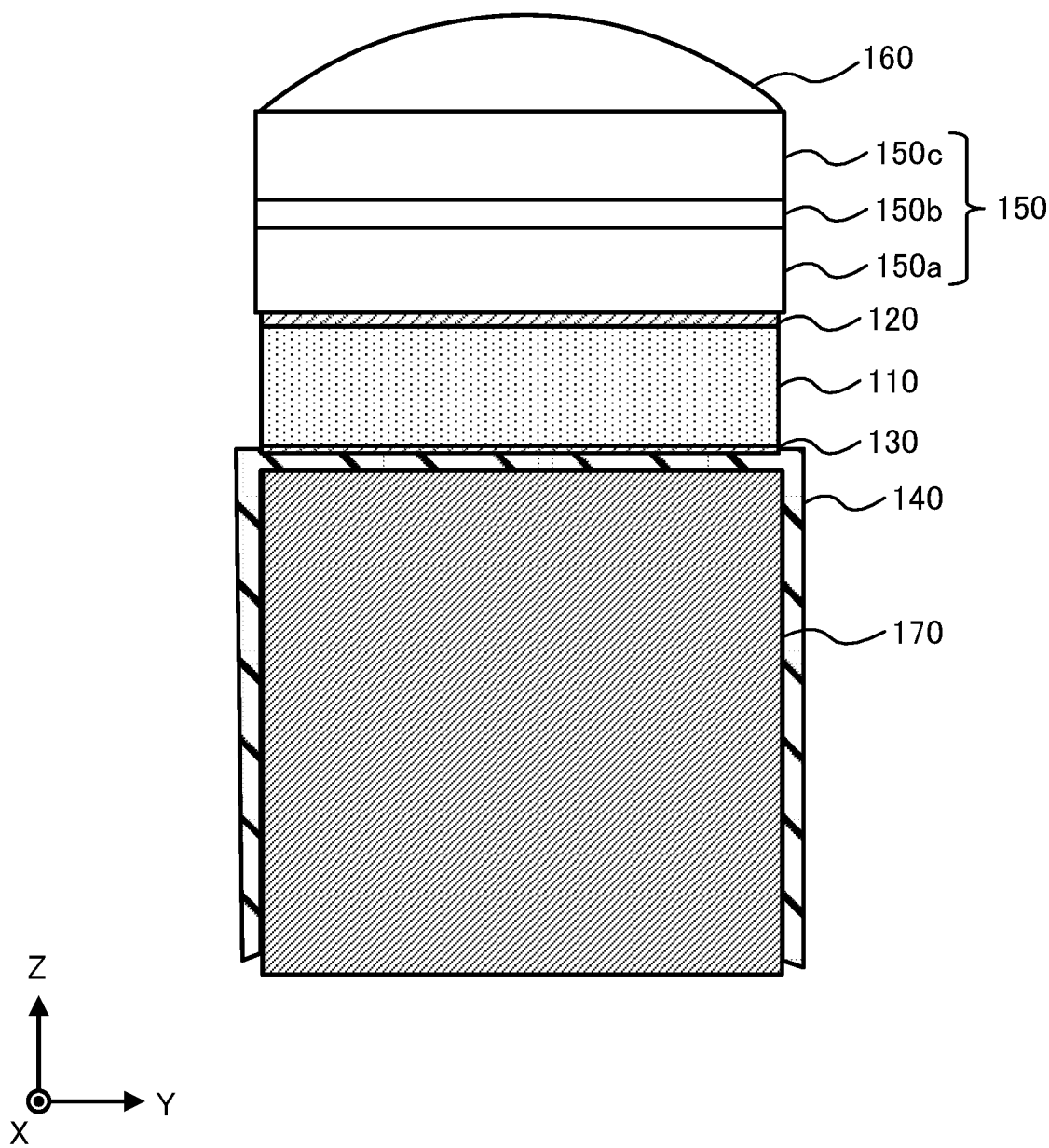
FIG. 1 is a schematic view showing an exemplary structure of an image forming apparatus according to an embodiment of the present invention.

FIG. 1 is a cross-sectional view showing one example of the entire structure of ultrasound probe 100 relating to an embodiment of the present invention.

As shown in FIG. 1, ultrasound probe 100 is composed of piezoelectric element 110, ground electrode 120 disposed on the front surface side and signal electrode 130 on the rear surface side to apply a voltage to piezoelectric element 110 and signal electric terminal 140, acoustic matching layer 150 and acoustic lens 160 disposed in the order mentioned on the front surface side from piezoelectric element 110, and backing material 170 disposed in the order mentioned on the rear surface side from signal electric terminal 140.

1-1. Piezoelectric Element

Piezoelectric element 110 is formed in such a manner that a plurality of piezoelectric bodies (not illustrated), which transmits ultrasound by application of a voltage, is arranged in one dimension in an X direction of FIG. 1. The thickness of piezoelectric element 110 can be set, for example, to 0.05 mm or more and 0.4 mm or less. Each of the piezoelectric bodies is formed by piezoelectric ceramic such as a lead zirconate titanate (PZT)-based ceramic, a piezoelectric single crystal such as a lead magnesium niobate-lead titanate solid solution (PMN-PT) and lead niobate zincate-lead titanate solid solution (PZN-PT), a composite piezoelectric body formed by those materials and a polymer material, and the like. The magnitude of the acoustic impedance of piezoelectric element 110 is usually 10 to 30 MRayls.

1-2. Ground Electrode, Signal Electrode, and Signal Electric Terminal

Ground electrode 120 is an electrode disposed on the front surface of piezoelectric element 110, and signal electrode 130 is an electrode disposed on the rear surface of piezoelectric element 110. Ground electrode 120 and signal electrode 130 can be formed by a method such as deposition or sputtering of gold, silver, or the like and silver sintering, or can be formed by bonding a conductor such as copper to an insulating substrate to be patterned, or the like. Signal electric terminal 140 is disposed in contact with the rear surface side of signal electrode 130 and connects signal electrode 130 and an external power supply or the like disposed on main body 11 of ultrasound diagnostic apparatus 10. In the present embodiment, signal electrode 130 is a flexible printed circuit (FPC) formed by bonding a conductor such as copper to an insulating substrate to be patterned.

1-3. Acoustic Matching Layer

Acoustic matching layer 150 is a layer for matching acoustic characteristics between piezoelectric element 110 and acoustic lens 160, and is formed by a material having an approximately intermediate acoustic impedance between piezoelectric element 110 and acoustic lens 160. In the present embodiment, acoustic matching layer 150 is formed by three layers of first acoustic matching layer 150a, second acoustic matching layer 150b, and third acoustic matching layer 150c.

Here, first acoustic matching layer 150a is formed by materials such as silicon, crystal, free-machining ceramics, graphite filled with metallic powder, and an epoxy resin filled with a filler such as a metal or an oxide, which materials have an acoustic impedance of 8 MRayls or more and 20 MRayls or less. Second acoustic matching layer 150b is formed by graphite and an epoxy resin filled with a filler such as a metal or an oxide, which have an acoustic impedance of 3 MRayls or more and 8 MRayls or less. Third acoustic matching layer 150c is formed by a plastic material mixed with a rubber material, a resin filled with a silicone rubber, and the like, having an acoustic impedance of 1.9 MRayls or more and 2.3 MRayls or less.

Multi-layering acoustic matching layer 150 as mentioned above can achieve broad-banding of the ultrasound probe. When acoustic matching layer 150 is multi-layered, it is more preferable to set an acoustic impedance of each layer such that the acoustic impedance gets gradually or continuously closer to the acoustic impedance of acoustic lens 160 as the acoustic matching layer approaches acoustic lens 160. Further, the layers of multi-layered acoustic matching layer 150 each may be bonded with an adhesive, which is generally used in the art, such as an epoxy-based adhesive.

The materials of acoustic matching layer 150 are not limited to the above-described materials, and known materials including aluminum, aluminum alloys, magnesium alloys, Macor glass, glass, fused quartz, copper graphite, resins, and the like can be used. Examples of the resins include polyethylene, polypropylene, polycarbonate, an ABS resin, an AAS resin, an AES resin, nylon, polyphenylene oxide, polyphenylene sulfide, polyphenylene ether, polyetheretherketone, polyamide imide, polyethylene terephthalate, an epoxy resin, and a urethane resin.

1-4. Acoustic Matching Layer

Acoustic lens 160 is formed, for example, by a soft polymer material or the like which has an acoustic impedance close to that of the living body and an acoustic velocity different from that of the living body, and acoustic lens 160 converges ultrasound transmitted from piezoelectric element 110 using refraction by use of a difference in acoustic velocity between the living body and acoustic lens 160 to improve a resolution. In the present embodiment, acoustic lens 160 is a cylindrical acoustic lens which extends along a Y direction in the drawing (a direction perpendicular to an arrangement direction X of the piezoelectric body) and is formed in a convex shape in a Z direction. Acoustic lens 160 converges the ultrasound in the Y direction to output the ultrasound outside ultrasound probe 100.

Examples of the soft polymer material include silicone rubbers.

1-5. Backing Material

Backing material 170 is a layer that holds piezoelectric element 110, simultaneously attenuates ultrasound transmitted from piezoelectric element 110 to the rear surface side, and radiates heat generated from piezoelectric element 110 to the rear surface side. Backing material 170 is usually formed by including a synthetic rubber, a natural rubber, an epoxy resin, a thermoplastic resin, or the like which is filled with a material for adjusting the acoustic impedance. The shape of backing material 170 is not particularly limited as long as it can attenuate the transmitted ultrasound.

Backing material 170 has an enhanced heat conductivity by containing heat conductive particles.

1-5-1. Heat Conductive Particles

The heat conductive particles are particles containing a heat conductive material. From the viewpoint of further enhancing the heat conduction of backing material 170 and facilitating adjustment of acoustic characteristics, the heat conductive material described above has a heat conductivity of preferably 60 to 5,000 w/mk, more preferably 200 to 3,000 w/mk, still more preferably 400 to 3,000 w/mk. Examples of the heat conductive material having a heat conductivity in the range described above include aluminum oxide, silicon carbide, aluminum nitride, silicon nitride, beryllium oxide, boron nitride, magnesium oxide, graphene, carbon nanotubes, aluminum, gold, silver, iron, and copper. The heat conductive particles may contain one of these heat conductive materials or may contain two or more of these. The heat conductive particles may contain a material other than the heat conductive material, as composite particles to be mentioned below.

Herein, that the acoustic characteristics of backing material 170 are good means that backing material 170 has a sufficiently high attenuation factor of ultrasound or backing material 170 has an acoustic impedance sufficient to moderately reflect ultrasound from piezoelectric element 110. It is preferred that backing material 170 have a sufficiently high attenuation factor of ultrasound and backing material 170 have an acoustic impedance sufficient to moderately reflect ultrasound from piezoelectric element 110.

Here, from the viewpoint of suppressing occurrence of a noise (artifact), the attenuation factor of the ultrasound described above is preferably higher. The value of the acoustic impedance described above can be raised when a clean waveform is desired at some expense of the sensitivity, or can be lowered when the sensitivity is desired to be raised. The shape of a band can be controlled by means of the value of the acoustic impedance. When the value of the acoustic impedance described above is low, the band broadens, and when the value of the acoustic impedance is high, the band narrows.

From the viewpoint of adjusting the orientation state of the heat conductive particles to thereby facilitate the adjustment of acoustic characteristics, the heat conductive material is preferably multi-layered (ML) graphene, silicon carbide, and carbon nanotubes.

The orientation state of the heat conductive particles is preferably adjusted such that aggregation is suppressed in backing material 170. This can suppress variations in the heat conductivity and acoustic characteristics in backing material 170, raise the heat conduction of backing material 170, and also make the acoustic characteristics of backing material 170 good.

When the number of heat conductive particles contained in backing material 170 is large, the durability of backing material 170 is likely to decrease, or the acoustic impedance of backing material 170 is likely to fall out of a suitable range.

From the viewpoint described above, the content of the heat conductive particles in backing material 170 is preferably less than 30 vol %, more preferably 4 vol % or more and 20 vol % or less, still more preferably 6 vol % or more and 15 vol % or less based on the total volume of backing material 170. As mentioned above, adjusting the amount of the heat conductive particles in a smaller range can control aggregation of the heat conductive particles.

From the viewpoint of suppressing aggregation of the heat conductive particles, the amount of the above heat conductive particles contained in backing material 170 is preferably smaller, whereas backing material 170 preferably contains the above heat conductive particles in an amount sufficient to suppress overheat of acoustic lens 160. Specifically, backing material 170 preferably has a heat conductivity of 2.0 W/mk or more, more preferably has a heat conductivity of 4.0 W/mk or more, still more preferably has a heat conductivity of 10.0 W/mk or more, particularly preferably has a heat conductivity of 20.0 W/mk or more, by containing the heat conductive particles.

However, according to the findings of the present inventors, merely increasing the amount of the heat conductive particles contained in backing material 170 only facilitates aggregation of the heat conductive particles, and thus, the heat conductivity of backing material 170 does not rise as expected. In order to efficiently enhance the heat conductivity of backing material 170, it is necessary to adjust the orientation state of the heat conductive particles to thereby disperse the heat conductive particles more suitably.

From the viewpoint of facilitating adjustment of the orientation state of the above heat conductive particles, the average particle size of the heat conductive particles is preferably 10 μm or more and 150 μm or less, more preferably 10 μm or more and 100 μm or less. When the average particle size of the heat conductive particles is in the above range, the heat conductive particles are more likely to disperse and the orientation state of the heat conductive particles is more likely to be adjusted, in comparison with the case where particles having a smaller average particle size are used. Herein, as the average particle size of the particles, a value determined using a laser-type particle size analyzer. Alternatively, herein, the average particle size of the particles contained in backing material 170 may be a value obtained by slicing backing material 170, imaging the sliced material by a transmission electron microscope at a magnification of about 1,000,000 to give an image, and analyzing the obtained image with known image analysis software.

1-5-1-1. Composite Particles

From the viewpoint of suppressing aggregation of the above heat conductive particles to thereby facilitate the adjustment of the orientation state, the heat conductive particles are preferably composite particles. Employing composite particles can reduce the particle concentration in an epoxy resin, and thus, the surface of the particles is more likely to be covered with the epoxy resin. For this reason, it is possible to suppress occurrence of air bubbles and cracks on molding backing material 170, and it is also possible to suppress a volume change on dicing.

The composite particles described above are particles obtained by combining particles formed of the heat conductive material mentioned above with a material other than these (for example, an elastomer). The composite particles may further contain a filler and the like.

The elastomer is a substance having rubber elasticity at room temperature. The elastomer may be a thermosetting elastomer or a thermoplastic elastomer.

Examples of the thermoplastic elastomer include polyester elastomers, polyamide elastomers, polyether elastomers, polyurethane elastomers, polyolefin elastomers, polystyrene elastomers, polyacrylic elastomers, polydiene elastomers, silicone-modified polycarbonate elastomers, and fluorine copolymer elastomers.

Examples of the thermosetting elastomer include flexible epoxy resins, silicone resins, isoprene rubbers, ethylene-propylene rubbers, butadiene rubbers, chloroprene rubbers, and natural rubbers.

Since ultrasound probes are disinfected under a high-temperature gas environment or the like, the elastomer is preferably a thermosetting elastomer unlikely to cause deformation, flowing, or the like in response to a temperature change, more preferably a silicone resin.

The composite particles may be produced by pulverizing a mixture of materials of the composite particles in a pulverizer. In this case, from the viewpoint of making the mixture more pulverizable to thereby facilitate production of the composite particles and from the viewpoint of suppressing occurrence of air bubbles and cracks due to breaking of the composite particles on molding of backing material 170, the elastomer is preferably a material having a short elongation on cutting and having lower hardness.

From the above viewpoints, the elastomer has a tensile breaking strength of preferably 3.0 MPa or less, more preferably 1.5 MPa or less. Also from the above viewpoints, the elastomer has a tensile breaking elongation of preferably 160% or less, more preferably 140% or less. The tensile breaking strength and the tensile breaking elongation of the elastomer can be values obtained by measurement in compliance with JIS K 6251 (2017). The lower limit value of the tensile breaking elongation is not particularly limited, but can be 30% or more.

From the above viewpoints, the elastomer has a hardness to be measured with a type A durometer of preferably 38 or less, more preferably 32 or less. The hardness of the elastomer can be a hardness obtained by measurement in compliance with JIS K 6253-1 (2012).

From the viewpoint of suppressing formation of two peaks in the particle size, which is caused by delamination between the elastomer and other material (the heat conductive material and a filler) during shearing on pulverization, the elastomer has an adhesive strength of preferably 0.3 MPa or more, more preferably 0.5 MPa or more. The adhesive strength of the elastomer can be a value obtained by measurement in compliance with JIS K 6256-1 (2013).

From the viewpoint of more enhancing adhesion to the above other material to thereby suppress formation of two peaks in the particle size due to the above delamination, the elastomer preferably contains a coupling agent, such as a silane coupling agent, a titanium coupling agent, and an aluminum coupling agent. When the elastomer is a silicone resin (particularly RTV (room temperature vulcanizing) silicone resin), from the viewpoint of further enhancing adhesion to the above other material, the coupling agent is preferably a coupling agent having a double bond in the molecule.

Examples of commercially available products of the silane coupling agent include KBM-1003, KBM-1403, KBM-502, KBM-503, KBE-1003, KBE502, KBE-503, and KBM-5103 (all manufactured by Shin-Etsu Chemical Co., Ltd.). Examples of commercially available products of the titanium coupling agent include PLENACT 55 and PLENACT TTS (both manufactured by Ajinomoto Fine-Techno Co., Inc., "PLENACT" is a registered trademark of Ajinomoto Co., Inc.), ORGATICS TC-100, ORGATICS TC-401, ORGATICS TC-710, and ORGATICS TC-120 (all manufactured by Matsumoto Fine Chemical Co., Ltd., "ORGATICS" is a registered trademark of the company). Examples of commercially available products of the aluminum coupling agent include PLENACT AL-M (manufactured by Ajinomoto Fine-Techno Co., Inc.).

From the viewpoint of increasing the density difference between the elastomer and the filler to thereby more increase the attenuation of ultrasound due to the composite particles, the elastomer preferably has a specific gravity of 1.1 or less. Combining such an elastomer with tungsten oxide (specific gravity: 7.16) or thermally expandable microcapsules (specific gravity of a commercially available product: for example, 0.03) can make scattering of ultrasound at an interface between the elastomer and the filler more likely to occur to thereby further increase the attenuation of ultrasound due to the composite particles.

Examples of the filler include inorganic particles and hollow particles. Examples of the above inorganic particles include ferrite, tungsten oxide, ytterbium oxide, bismuth oxide, zinc oxide, zirconium oxide, tin oxide, nickel oxide, barium oxide, manganese oxide, yttrium oxide, indium oxide, tantalum oxide, and barium titanate. Examples of the above hollow particles include glass balloons, hollow silica, Cenolite, phenolic resin microballoons, urea resin microballoons, and polymethyl methacrylate balloons, and thermally expandable microcapsules. One of the above fillers may be used singly or two or more of the fillers may be used in combination.

The above composite particles can be prepared by conventionally known various methods.

The density of the heat conductive particles as the composite particles is preferably 1.0 to 3.5 g/cm$^3$, more preferably 1.5 to 3.0 g/cm$^3$. When the density of the composite particles is within the above range, the acoustic impedance of the backing material is more likely to be controlled to a desired range even when the amount of the composite particles added is small.

The average particle size of the heat conductive particles as the composite particles is preferably 100 to 350 μm, more preferably 150 to 250 μm. When the average particle size of the heat conductive particles is in the above range, the heat conductive particles are more likely to disperse and the orientation state of the heat conductive particles is more likely to be adjusted, in comparison with the case where particles having a smaller average particle size are used.

1-5-2. Non-Heat Conductive Particles

Backing material 170 may contain non-heat conductive particles in addition to the heat conductive particles, from the viewpoint of adjusting the orientation state of the heat conductive particles to thereby facilitate adjustment of acoustic characteristics. Particularly, when backing material 170 contains non-heat conductive particles having a relatively large particle size, it is possible to arrange the heat conductive particles along the interface of the non-heat conductive particles. This forms a heat transfer path by means of the heat conductive particles, and thus can efficiently enhance the heat conductivity of backing material 170 even if the amount of the heat conductive particles is small. This also suppresses aggregation of the heat conductive particles and also suppresses variations in the acoustic characteristics of backing material 170. Arranging the heat conductive particles along the interface of the non-heat conductive particles can suppress formation of aggregates by the heat conductive particles with one another. Thus, it is possible to suppress occurrence of air bubbles and cracks on molding of backing material 170, to enhance the durability of backing material 170, and also to suppress a volume change on dicing.

From the viewpoint of facilitating an arrangement of the heat conductive particles along the interface of the non-heat conductive particles, the average particle size of the non-heat conductive particles is preferably 100 to 350 μm, more preferably 150 to 250 μm.

Also from the viewpoint of facilitating the arrangement of the heat conductive particles along the interface of the non-heat conductive particles, the ratio of the total volume of the heat conductive particles to the total volume of the non-heat conductive particles contained in backing material 170 (the total volume of the heat conductive particles/the total volume of the non-heat conductive particles) is preferably 1/10 or more and 1/1 or less, more preferably 1/5 or more and 1/2 or less.

The content of the non-heat conductive particles in backing material 170 is preferably 30 vol % or more and 45 vol % or less based on the total volume of backing material 170.

From the viewpoint of facilitating adjustment of the acoustic characteristics of backing material 170, the non-heat conductive particles are preferably composite particles.

The non-heat conductive particles as the composite particles can be configured in the same manner as for the non-heat conductive particles as the composite particles mentioned above, except for containing no heat conductive material.

1-5-3. Base Material (Matrix Resin)

Backing material 170 contains a matrix resin as a base material. The heat conductive particles and non-heat conductive particles are dispersed in the above matrix resin.

The matrix resin may be a thermosetting resin such as synthetic rubber, natural rubber, or an epoxy resin, or may be a thermoplastic resin such as polyethylene. Among these, from the viewpoint of further enhancing the heat resistance of backing material 170, the matrix resin is preferably a thermosetting resin, more preferably an epoxy resin.

Examples of the epoxy resin include bisphenol type epoxy resins such as bisphenol A type and bisphenol F type, novolac type epoxy resins such as resol novolac type and phenol-modified novolac type, polycyclic aromatic epoxy resins such as naphthalene structure-containing type, anthracene structure-containing type, and fluorene structure-containing type, hydrogenated alicyclic epoxy resins, and liquid-crystalline epoxy resins. One of the above epoxy resins may be used singly or two or more of the epoxy resins may be used in combination.

The thermosetting resin may be a liquid or powder. Of these, from the viewpoint of temporarily fixing the above heat conductive particles in a dispersed state to thereby suppress aggregation of the heat conductive particles in backing material 170 and facilitate adjustment of the orientation state of the particles, the thermosetting resin is preferably a powder. When the thermosetting resin is a powder, it is possible to suppress aggregation of the heat conductive particles to thereby facilitate adjustment of the orientation state also in the case where materials are each mixed on producing backing material 170.

When the thermosetting resin is a powder, its glass transition temperature (Tg) is preferably 100° C. or more and 200° C. or less. When Tg of the thermosetting resin is within the above range, the thermosetting resin can maintain a predetermined hardness even in the case where ultrasound probe 100 is used and the temperature inside the probe rises to about 50° C. to 60° C. For this reason, it is possible to suppress deterioration of backing material 170 due to flowing of the particles inside the base material caused by softening of the base material, and the like. Additionally, when the Tg of the thermosetting resin is within the above range, it is possible to harden backing material 170 to the extent that the material can be easily cut and it is possible to make the brittleness of backing material 170 lower to the extent that the material does not break during cutting, on processing backing material 170.

The content of the matrix resin in backing material 170 is preferably 40 vol % or more and 64 vol % or less based on the total volume of backing material 170.

1-5-4. Method for Preparing Backing Material

Backing material 170 can be prepared by a method including mixing the matrix resin and the heat conductive resin to prepare a mixture and molding the mixture.

The mixture is only required to contain the matrix resin, the heat conductive particles, the non-heat conductive particles, and other additives at a ratio corresponding to the composition of backing material 170 mentioned above.

For example, the mixture can be a mixture that contains the heat conductive particles of less than 30 vol % based on the total volume thereof and has a heat conductivity of 2.0 W/mk or more.

Alternatively, the mixture may be a mixture containing the matrix resin, the heat conductive resin, and the non-heat conductive particles.

Alternatively, the mixture may be a mixture containing the matrix resin as a powder and the heat conductive resin.

When the matrix resin is a liquid, for example, the mixture can be molded into a shape of backing material 170 by injecting the mixture into a mold, sufficiently defoaming the mixture, and heating the mixture after stirring.

When the matrix resin is a powder, the mixture can be molded into a shape of backing material 170 by introducing the sufficiently mixed mixture into a mold and pressurizing and heating the mixture under vacuum-degassing.

When the matrix resin is a thermosetting resin, it is preferred to add a curing agent to the mixture. Examples of the above curing agent include chain aliphatic polyamines such as diethylene triamine, triethylene tetramine, dipropylene diamine, and diethylaminopropylamine; cyclic aliphatic polyamines such as N-aminoethylpiperazine, mensendiamine, and isophoronediamine; aromatic amines such as m-xylenediamine, meta-phenylenediamine, diaminodiphenylmethane, and diaminodiphenylsulfone; polyamide resins; secondary and tertiary amines such as piperidine, N,N-dimethylpiperazine, triethylenediamine, 2,4,6-tris(dimethylaminomethyl)phenol, benzyldimethylamine, and 2-(dimethylaminomethyl)phenol; imidazoles such as 2-methylimidazole, 2-ethylimidazole, and 1-cyanoethyl-2-undecyl imidazolium trimellitate; liquid polymercaptans and polysulfides; and acid anhydrides such as phthalic anhydride, trimellitic anhydride, methyltetrahydrophthalic anhydride, methyl endomethylene tetrahydrophthalic anhydride, methylbutenyl tetrahydrophthalic anhydride, and methylhexahydrophthalic anhydride. One of the curing agents may be used singly or two or more curing agents may be used in combination.

2. Ultrasound Diagnostic Apparatus

Figure 2:
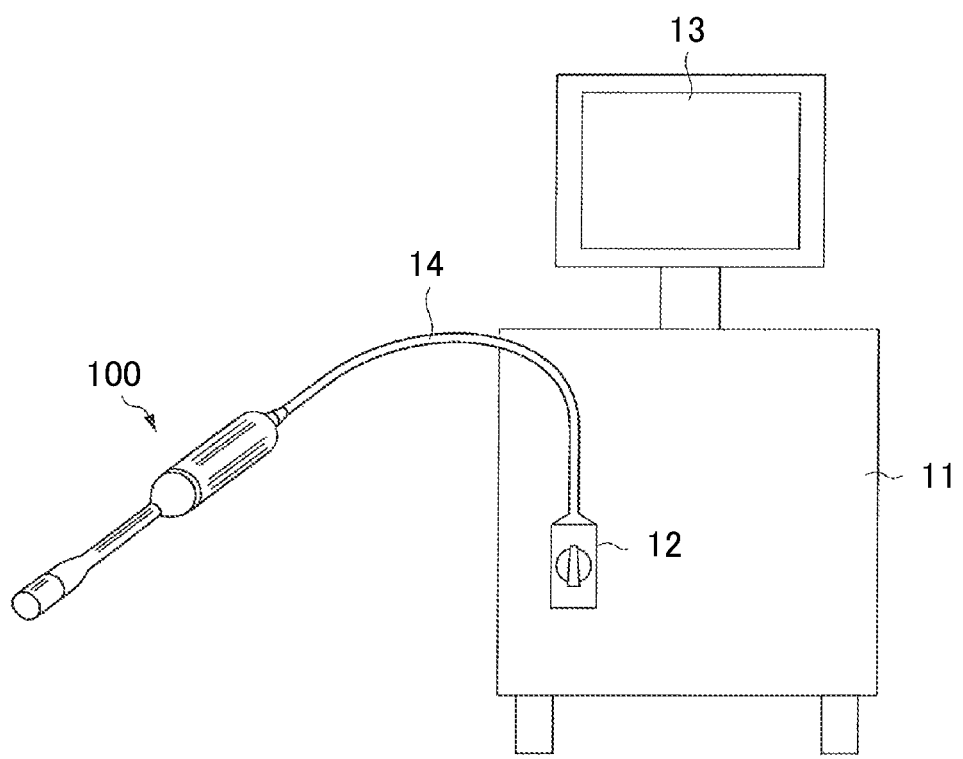
FIG. 2 is a schematic view showing one example of an ultrasound diagnostic apparatus including an ultrasound probe according to the embodiment of the present invention.

FIG. 2 is a schematic view showing one example of ultrasound diagnostic apparatus 10 including ultrasound probe 100. Ultrasound diagnostic apparatus 10 includes ultrasound probe 100, main body 11, connector section 12, and display 13.

Ultrasound probe 100 is connected to ultrasound diagnostic apparatus 10 through cable 14 connected to connector section 12.

The electric signal (transmission signal) from ultrasound diagnostic apparatus 10 is transmitted to piezoelectric element 110 of ultrasound probe 100 through cable 14. This transmission signal is converted into ultrasound in piezoelectric element 110 and the ultrasound is transmitted into the living body. The transmitted ultrasound is reflected by tissues or the like in the living body, some of reflected waves are also received in piezoelectric element 110 to be converted into an electric signal (reception signal), and the electric signal is transmitted to main body 11 of ultrasound diagnostic apparatus 10. The reception signal is converted into image data in main body 11 of ultrasound diagnostic apparatus 10 and the image data is displayed on display 13.

The ultrasound diagnostic apparatus of the present invention, which has the ultrasound probe of the present invention, can generate an ultrasound image having a favorable image quality.

Examples

Hereinbelow, the present invention will be described more specifically using the following tests, but the present invention is not limited to the following tests.

1. Preparation of Composite Particles

Non-thermoplastic particles as composite particles and thermoplastic particles as composite particles were prepared using the following materials.

(Elastomer)

Main agent 1: TSE3032(A) (manufactured by Momentive Performance Materials Inc., thermo-curing type liquid silicone rubber)

Curing agent 1: TSE3032(B)

Main agent 2: TSE3033(A) (manufactured by Momentive Performance Materials Inc., thermo-curing type liquid silicone rubber)

Curing agent 2: TSE3033(B)

(Filler)

Filler 1: A2-$WO_3$ (manufactured by A.L.M.T. Corp., tungsten trioxide powder)

Filler 2: C3-$WO_3$ (manufactured by A.L.M.T. Corp., tungsten trioxide powder)

Filler 3: Expancel 920DE40d30 (manufactured by Japan Fillite Co., Ltd., thermally expandable microcapsule)

Filler 4: Expancel 920 (manufactured by Japan Fillite Co., Ltd., thermally expandable microcapsule)

With respect to an elastomer obtained by reacting main agent 1 with curing agent 1, the tensile breaking strength to be obtained by measurement in compliance with JIS K 6251 (2017) is 4.5 MPa, the tensile breaking elongation obtained by measurement in compliance with JIS K 6251 (2017) is 210%, and the hardness to be measured by a type A durometer is 35.

With respect to an elastomer obtained by reacting main agent 2 with curing agent 2, the tensile breaking strength to be obtained by measurement in compliance with JIS K 6251 (2017) is 1.0 MPa, the tensile breaking elongation obtained by measurement in compliance with JIS K 6251 (2017) is 130%, and the hardness to be measured by a type A durometer is 30.

(Particles Constituted by Heat Conductive Material)

Particles 1: SSC-A30 (manufactured by Shinano Electric Refining Co., Ltd. spherical silicon carbide)

Particles 2: iGrafen-α (manufactured by ITEC Co., Ltd., multi-layered graphene)

1-1. Composite Particles 1

To 100 parts by mass of main agent 1, 803 parts by mass of filler 1 was added, and the components were sufficiently mixed in a vacuum mixer "ARV-310" (manufactured by THINKY CORPORATION). Then, 10 parts by mass of curing agent 1 was added thereto and mixed well to obtain mixture 1.

Mixture 1 was placed in a metal mold of 100 mm×100 mm×30 mm, left to stand in a vacuum electric heating press at a pressure of 4.9 MPa (50 kg/$cm^2$) under vacuum, at room temperature for 3 hours, and then heated at 50° C. for 3 hours to prepare block 1. The density of block 1 was 4.07 g/$cm^3$. Block 1 was cut into 1-cm cubes, and the cubes were roughly milled in a cutter mill "VM-20" (manufactured by MAKINO mfg. co., ltd.). Then, main milling was performed in a pin mill "M-4" (manufactured by Nara Machinery Co., Ltd.) using a screen of 0.5 mm at a rotational speed of 2,800 rpm. In the end, the milled product was sieved in a circular vibrating screen apparatus "KG-400" (manufactured by Nishimura Machine Works Co., Ltd., opening size: 212 µm) to obtain composite particles 1 as non-heat conductive particles.

The particle size distribution of composite particles 1 was measured using a laser-type particle size analyzer (LMS-30 (manufactured by Seishin Enterprise Co., Ltd.)) and isopropyl alcohol as a dispersion medium for measurement, with the optimal point of the scattered intensity adjusted, under stirring and ultrasound dispersion. As a result of the particle size measurement, the average particle size was 112 µm, and there was no peak particle size of 30 µm or less.

1-2. Composite Particles 2

To 50 parts by mass of main agent 2, 365 parts by mass of filler 2 and 1.53 parts by mass of filler 3 were added, and the components were sufficiently mixed in a vacuum mixer. Then, 50 parts by mass of curing agent 2 was added thereto and mixed well to obtain mixture 2.

Mixture 2 was placed in a metal mold of 100 mm×100 mm×30 mm, left to stand in a vacuum electric heating press at a pressure of 4.9 MPa (50 kg/$cm^2$) under vacuum, at room temperature for 3 hours, and then heated at 50° C. for 3 hours to prepare block 2. The density of block 2 was 2.29 g/$cm^3$. Block 2 was cut into 1-cm cubes, and the cubes were roughly milled in the above cutter mill. Then, main milling was performed in the above pin mill using a screen of 0.5 mm at a rotational speed of 2,800 rpm. In the end, the milled product was sieved in the above circular vibrating screen apparatus (opening size: 212 µm) to obtain composite particles 2 as non-heat conductive particles. As a result of the average particle size measurement in the same manner as for composite particles 1, the average particle size was 251 µm.

1-3. Composite Particles 3

To 50 parts by mass of main agent 2, 320 parts by mass of particles 3 were added, and the components were sufficiently mixed in a vacuum mixer. Then, 50 parts by mass of curing agent 2 was added thereto and mixed well to obtain mixture 3.

Mixture 3 was placed in a metal mold of 100 mm×100 mm×30 mm, left to stand in a vacuum electric heating press at a pressure of 4.9 MPa (50 kg/$cm^2$) under vacuum, at room temperature for 3 hours, and then heated at 50° C. for 3 hours to prepare block 3. The density of block 3 was 2.12 g/cm³. Block 3 was cut into 1-cm cubes, and the cubes were roughly milled in the above cutter mill. Then, main milling was performed in the above pin mill using a screen of 0.5 mm at a rotational speed of 2,800 rpm. In the end, the milled product was sieved in the above circular vibrating screen apparatus (opening size: 212 μm) to obtain composite particles 3 as heat conductive particles. As a result of the average particle size measurement in the same manner as for composite particles 1, the average particle size was 248 μm.

1-4. Composite Particles 4

To 100 parts by mass of main agent 1, 266 parts by mass of filler 2, 1.11 parts by mass of filler 3, and 47.3 parts by mass of particles 2 were added, and the components were sufficiently mixed in a vacuum mixer. Then, 10 parts by mass of curing agent 1 was placed thereto and mixed well to obtain mixture 4.

Mixture 4 was placed in a metal mold of 100 mm×100 mm×30 mm, left to stand in a vacuum electric heating press at a pressure of 4.9 MPa (50 kg/cm²) under vacuum, at room temperature for 3 hours, and then heated at 50° C. for 3 hours to prepare block 4. The density of block 4 was 2.04 g/cm³. Block 4 was cut into 1-cm cubes, and the cubes were roughly milled in the above cutter mill. Then, main milling was performed in the above pin mill using a screen of 0.5 mm at a rotational speed of 2,800 rpm. In the end, the milled product was sieved in the above circular vibrating screen apparatus (opening size: 212 μm) to obtain composite particles 4 as heat conductive particles. As a result of the average particle size measurement in the same manner as for composite particles 1, the average particle size was 210 μm.

1-5. Composite Particles 5

To 50 parts by mass of main agent 2, 242 parts by mass of filler 2, 1.01 parts by mass of filler 4, and 43 parts by mass of particles 2 were added, and the components were sufficiently mixed in a vacuum mixer. Then, 50 parts by mass of curing agent 2 was placed thereto and mixed well to obtain mixture 5.

Mixture 5 was placed in a metal mold of 100 mm×100 mm×30 mm, left to stand in a vacuum electric heating press at a pressure of 4.9 MPa (50 kg/cm²) under vacuum, at room temperature for 3 hours, and then heated at 50° C. for 3 hours to prepare block 5. The density of block 5 was 2.04 g/cm³. Block 5 was cut into 1-cm cubes, and the cubes were roughly milled in the above cutter mill. Then, main milling was performed in the above pin mill using a screen of 0.5 mm at a rotational speed of 2,800 rpm. In the end, the milled product was sieved in the above circular vibrating screen apparatus (opening size: 212 μm) to obtain composite particles 5 as heat conductive particles. As a result of the average particle size measurement in the same manner as for composite particles 1, the average particle size was 234 μm.

The composition, density, and average particle size of composite particles 1 to 5 are shown in Table 1.

TABLE 1

| | Elastomer | | | | Filler | | | | Heat conductive particles | | Density g/cm³ | Average particle size μm |
| | Main agent | | Curing agent | | | | | | | | | |
| | Type | Parts by mass | Type | Parts by mass | Type | Parts by mass | Type | Parts by mass | Type | Parts by mass | | |
|---|---|---|---|---|---|---|---|---|---|---|---|---|
| Composite particles 1 | Main agent 1 | 100 | Curing agent 1 | 10 | Filler 1 | 803 | — | — | — | — | 4.07 | 112 |
| Composite particles 2 | Main agent 2 | 50 | Curing agent 2 | 50 | Filler 2 | 365 | Filler 3 | 1.53 | — | — | 2.29 | 251 |
| Composite particles 3 | Main agent 2 | 50 | Curing agent 2 | 50 | — | — | — | — | Particles 3 | 320 | 2.12 | 248 |
| Composite particles 4 | Main agent 1 | 100 | Curing agent 1 | 10 | Filler 2 | 266 | Filler 3 | 1.11 | Particles 2 | 47.3 | 2.04 | 210 |
| Composite particles 5 | Main agent 2 | 50 | Curing agent 2 | 50 | Filler 2 | 242 | Filler 4 | 1.01 | Particles 2 | 43 | 2.04 | 234 |

2. Preparation of Backing Material

A backing material was prepared using the following materials.

(Matrix Resin)

Main agent 3: Albidur EP2240 (manufactured by Evonik Industries, liquid epoxy resin)

Curing agent 3: jER Cure ST-12 (manufactured by Mitsubishi Chemical Corporation)

Main agent 4: jER 828 (manufactured by Mitsubishi Chemical Corporation, liquid epoxy resin)

Curing agent 4: jER Cure 113 (manufactured by Mitsubishi Chemical Corporation)

Main agent 5: PCE-751 (manufactured by Pelnox Limited, powder epoxy resin)

(Non-Heat Conductive Particles)

Composite particles 1: composite particles 1 prepared as described above

Composite particles 2: composite particles 2 prepared as described above

Particles 1: X-52-875: (manufactured by Shin-Etsu Chemical Co., Ltd., silicone rubber particles)

(Heat Conductive Particles)

Particles 2: iGrafen-α (manufactured by ITEC Co., Ltd., multi-layered graphene)

Particle 3: SSC-A30 (manufactured by Shinano Electric Refining Co., Ltd. spherical silicon carbide)

Particles 4: FloTube 9000 (manufactured by CNano Technology, multi-layered carbon nanotubes)

Composite particles 3: composite particles 3 prepared as described above

Composite particles 4: composite particles 4 prepared as described above

Composite particles 5: composite particles 5 prepared as described above

The heat conductivity of the heat conductive material constituting particles 3 and composite particles 3 (silicon carbide) is 270 W/mk, the heat conductivity of the heat conductive material constituting particles 2, composite particles 4, and composite particles 5 (multi-layered graphene) was 1,300 W/mk, and the heat conductivity of the heat conductive material constituting particles 4 (multi-layered carbon nanotubes) is 2,000 W/mk.

The density of particles 1 is 0.97 g/cm$^3$, the density of particles 2 is 2.2 g/cm$^3$, the density of particles 3 is 3.2 g/cm$^3$, and the density of particles 4 is 2.2 g/cm$^3$.

2-1. Backing Material 1

Sufficiently mixed were 76.0 parts by mass of main agent 3 and 730 parts by mass of composite particles 1 in a vacuum mixer. Further, 24.0 parts by mass of curing agent 3 was added thereto and further mixed to obtain a compound.

The above compound was placed in a metal mold of 100 mm×100 mm×30 mm, left to stand in a vacuum electric heating press "OHV-H" (manufactured by Oji Machine Co., Ltd.) under application of a pressure of 9.9 MPa (100 kg/cm$^2$) at room temperature for 4 hours, and then heated at 80° C. for 3 hours to obtain backing material 1.

2-2. Backing Material 2

Sufficiently mixed were 76.0 parts by mass of main agent 3 and 97.0 parts by mass of particles 2 in a vacuum mixer. Further, 24.0 parts by mass of curing agent 3 was added thereto and further mixed to obtain a compound.

The above compound was placed in a metal mold of 100 mm×100 mm×30 mm, left to stand in the above vacuum electric heating press under application of a pressure of 9.9 MPa (100 kg/cm$^2$) at room temperature for 4 hours, and then heated at 80° C. for 3 hours to obtain backing material 2.

2-3. Backing Material 3

Backing material 3 was obtained in the same manner as for backing material 2 except that the content of each component was changed.

2-4. Backing Material 4

Sufficiently mixed were 75.8 parts by mass of main agent 4, 83.0 parts by mass of composite particles 2, and 13.8 parts by mass of particles 2 in a vacuum mixer. Further, 24.2 parts by mass of curing agent 4 was placed thereto and further mixed to obtain a compound.

The above compound was placed in a metal mold of 100 mm×100 mm×30 mm, left to stand in the above vacuum electric heating press under application of a pressure of 9.9 MPa (100 kg/cm$^2$) at 80° C. for 1 hour, and then heated at 150° C. for 3 hours to obtain backing material 4.

2-5. Backing Material 5

Backing material 5 was obtained in the same manner as for backing material 4 except that the amount of each component added was changed.

2-6. Backing Material 6

Backing material 6 was obtained in the same manner as for backing material 4 except that the amount of the non-heat conductive particles added was changed from 83.0 parts by mass to 95.0 parts by mass and the heat conductive particles were changed from particles 2 (13.8 parts by mass) to particles 3 (153.0 parts by mass)

2-7. Backing Material 7

Backing material 7 was obtained in the same manner as for backing material 4 except that the non-heat conductive particles were changed from composite particles 2 (83.0 parts by mass) to particles 1 (42.0 parts by mass) and the amount of particles 2 added was changed from 13.8 parts by mass to 26.0 parts by mass 2-8. Backing Material 8

Sufficiently mixed were 76.0 parts by mass of main agent 3 and 250.0 parts by mass of composite particles 3 in a vacuum mixer. Further, 24.0 parts by mass of curing agent 3 was placed thereto and further mixed to obtain a compound.

The above compound was placed in a metal mold of 100 mm×100 mm×30 mm, left to stand in the above vacuum electric heating press under application of a pressure of 9.9 MPa (100 kg/cm$^2$) at 80° C. for 1 hour, and then heated at 150° C. for 3 hours to obtain backing material 8.

2-9. Backing Material 9

Sufficiently mixed were 76.0 parts by mass of main agent 3 and 210.0 parts by mass of composite particles 4 in a vacuum mixer. Further, 24.0 parts by mass of curing agent 3 was placed thereto and further mixed to obtain a compound.

The above compound was placed in a metal mold of 100 mm×100 mm×30 mm, left to stand in the above vacuum electric heating press under application of a pressure of 9.9 MPa (100 kg/cm$^2$) at 80° C. for 1 hour, and then heated at 150° C. for 3 hours to obtain backing material 9.

2-10. Backing Material 10

Sufficiently mixed were 75.8 parts by mass of main agent 4 and 210.0 parts by mass of composite particles 4 in a vacuum mixer. Further, 24.2 parts by mass of curing agent 4 was added thereto and further mixed to obtain a compound.

The above compound was placed in a metal mold of 100 mm×100 mm×30 mm, left to stand in the above vacuum electric heating press under application of a pressure of 9.9 MPa (100 kg/cm$^2$) at room temperature for 4 hours, and then heated at 80° C. for 3 hours to obtain backing material 10.

2-11. Backing Material 11

Backing material 11 was obtained in the same manner as for backing material 10 except that composite particles 4 was replaced by composite particles 5.

2-12. Backing Material 12

Sufficiently mixed were 75.8 parts by mass of main agent 4 and 16.5 parts by mass of particles 2 in a vacuum mixer. Further, 24.2 parts by mass of curing agent 4 was added thereto and further mixed to obtain a compound.

The above compound was placed in a metal mold of 100 mm×100 mm×30 mm, left to stand in the above vacuum electric heating press under application of a pressure of 9.9 MPa (100 kg/cm$^2$) at room temperature for 4 hours, and then heated at 80° C. for 3 hours to obtain backing material 12.

2-13. Backing Material 13

Sufficiently mixed were 100 parts by mass of main agent 5, 83.0 parts by mass of composite particles 2, and 15.5 parts by mass of particles 2 in a vacuum mixer to obtain a compound.

The above compound was placed in a metal mold of 100 mm×100 mm×30 mm and heated in a vacuum electric heating press under application of a pressure of 9.9 MPa (100 kg/cm$^2$) at 150° C. for 2 hours to obtain backing material 13.

2-14. Backing Material 14

Backing material 14 was obtained in the same manner as for backing material 13 except that the amount of composite particles 2 added was changed from 83.0 parts by mass to 110.0 parts by mass and particles 2 (15.5 parts by mass) were replaced by particles 4 (13.0 parts by mass).

2-15. Backing Material 15

Backing material 15 was obtained in the same manner as for backing material 13 except that composite particles 2 (83.0 parts by mass) were replaced by composite particles 5 (125.0 parts by mass) and particles 2 (15.5 parts by mass) were replaced by particles 4 (8.5 parts by mass)

2-16. Backing Material 16

Sufficiently mixed were 100 parts by mass of main agent 5, 100.0 parts by mass of composite particles 4, and 17.0 parts by mass of particles 2 in a vacuum mixer to obtain a compound.

The above compound was placed in a metal mold of 100 mm×100 mm×30 mm and heated in a vacuum electric heating press under application of a pressure of 9.9 MPa (100 kg/cm$^2$) at 150° C. for 2 hours to obtain backing material 16.

The composition and the ratio of the volume of the heat conductive particles to the total volume of the non-heat conductive particles of backing materials 1 to 16 are shown in Table 2.

3-3. Heat Conductivity

The heat conductivity was determined in compliance with ASTM E1530. Specifically, the heat conductivity of backing materials 1 to 16 (specimen size: ϕ50 mm, t=10 mm (2 to 20 mm)) was measured using DTC-300 (manufactured by TA Instruments).

The physical properties of backing materials 1 to 16 are each shown in Table 3.

TABLE 2

| No. | Base agent Main agent Type | Parts by mass | Base agent Curing agent Type | Parts by mass | Non-heat conductive particles Type | Parts by mass | Non-heat conductive particles (Composite particles) Type | Parts by mass | Heat conductive particles Type | Parts by mass | Heat conductive particles (Composite particles) Type | Parts by mass | Content of heat conductive particles (vol %) | Heat conductive particles/Non-heat conductive particles (Volume ratio) |
|---|---|---|---|---|---|---|---|---|---|---|---|---|---|---|
| 1 | Main agent 3 | 76.0 | Curing agent 3 | 24.0 | — | — | Composite particle 1 | 730.0 | — | — | — | — | 0.0 | — |
| 2 | Main agent 3 | 76.0 | Curing agent 3 | 24.0 | — | — | — | — | Particles 2 | 97.0 | — | — | 35.0 | — |
| 3 | Main agent 3 | 76.0 | Curing agent 3 | 24.0 | — | — | — | — | Particles 2 | 77.0 | — | — | 29.6 | — |
| 4 | Main agent 4 | 75.8 | Curing agent 4 | 24.2 | — | — | Composite particle 2 | 83.0 | Particles 2 | 13.8 | — | — | 5.0 | 0.17 |
| 5 | Main agent 4 | 75.8 | Curing agent 4 | 24.2 | — | — | Composite particle 2 | 120.0 | Particles 2 | 35.0 | — | — | 10.5 | 0.30 |
| 6 | Main agent 4 | 75.8 | Curing agent 4 | 24.2 | — | — | Composite particle 2 | 95.0 | Particles 3 | 153.0 | — | — | 28.5 | 1.15 |
| 7 | Main agent 4 | 75.8 | Curing agent 4 | 24.2 | Particles 1 | 42.0 | — | — | Particles 2 | 26.0 | — | — | 8.5 | 0.27 |
| 8 | Main agent 3 | 76.0 | Curing agent 3 | 24.0 | — | — | — | — | — | — | Composite particle 3 | 250.0 | 29.2 | — |
| 9 | Main agent 3 | 76.0 | Curing agent 3 | 24.0 | — | — | — | — | — | — | Composite particle 4 | 210.0 | 5.7 | — |
| 10 | Main agent 4 | 75.8 | Curing agent 4 | 24.2 | — | — | — | — | — | — | Composite particle 4 | 210.0 | 5.7 | — |
| 11 | Main agent 4 | 75.8 | Curing agent 4 | 24.2 | — | — | — | — | Particles 3 | 16.5 | Composite particle 5 | 210.0 | 5.7 | — |
| 12 | Main agent 4 | 75.8 | Curing agent 4 | 24.2 | — | — | — | — | Particles 2 | 16.5 | Composite particle 4 | 100.0 | 9.2 | — |
| 13 | Main agent 5 | 100.0 | — | — | — | — | Composite particle 2 | 83.0 | Particles 2 | 15.5 | — | — | 5.8 | 0.19 |
| 14 | Main agent 5 | 100.0 | — | — | — | — | Composite particle 2 | 110.0 | Particles 4 | 13.0 | — | — | 4.3 | 0.12 |
| 15 | Main agent 5 | 100.0 | — | — | — | — | — | — | Particles 4 | 8.5 | Composite particle 5 | 125.0 | 7.0 | — |
| 16 | Main agent 5 | 100.0 | — | — | — | — | — | — | Particles 2 | 17.0 | Composite particle 4 | 100.0 | 9.3 | — |

3. Physical Properties of Backing Materials

The physical properties of backing materials 1 to 16 (acoustic impedance, attenuation, and heat conductivity) were each measured by the following method.

3-1. Acoustic Impedance

The acoustic impedance was measured in compliance with JIS Z2353-2003. Specifically, the acoustic impedance was measured using a sing-around type sound velocity measurement apparatus (manufactured by Ultrasonic Engineering Co., Ltd.) at 25° C., and the acoustic impedance was calculated in accordance with the following expression (1).

Acoustic impedance ($Z$: Mrayls)=density ($\rho$: ×10$^3$ kg/m$^3$)×sound velocity ($C$: ×10$^3$ msec)     Expression (1)

3-2. Attenuation

The attenuation of ultrasound was determined in compliance with JIS Z2354-1992. Specifically, a water tank was filled with water at 25° C., and an Ultrasonic Pulser & Receiver "JPR-10C" (manufactured by JAPAN PROBE CO., LTD.) was used to generate 1-MHz ultrasound in water and measure the magnitude of the amplitude of the ultrasound before and after the ultrasound penetrated a sheet.

TABLE 3

| | Physical properties | | |
|---|---|---|---|
| Backing | Acoustic impedance (Mrayls) | Attenuation (dB/mm · MHz) | Heat conductivity (W/mk) |
| 1 | 2.76 | 8.4 | 0.5 |
| 2 | 4.06 | 3.6 | 6.3 |
| 3 | 3.03 | 3.1 | 4.5 |
| 4 | 2.17 | 6.0 | 3.1 |
| 5 | 2.33 | 7.8 | 4.3 |
| 6 | 3.20 | 5.4 | 2.2 |
| 7 | 1.79 | 3.2 | 2.1 |
| 8 | 2.01 | 3.5 | 2.3 |
| 9 | 1.67 | 10.5 | 2.9 |
| 10 | 2.49 | 9.8 | 2.6 |
| 11 | 2.45 | 11.7 | 2.9 |
| 12 | 2.76 | 6.5 | 2.6 |
| 13 | 2.25 | 11.0 | 25.0 |
| 14 | 2.48 | 10.5 | 27.6 |
| 15 | 2.67 | 10.7 | 29.5 |
| 16 | 2.78 | 9.7 | 28.9 |

It was found that backing materials 8 to 11 containing the heat conductive particles as composite particles exhibited an attenuation equivalent or superior to that of backing materials 2 and 3 containing heat conductive particles that were not composite particles. It is conceived that this is because use of composite particles as the heat conductive particles enabled orientation of the particles to be easily controlled. For this reason, even in the case where the content of the heat conductive particles is reduced, a high attenuation can be obtained. Here, the larger the attenuation of the backing material, the lesser the reflection of ultrasound from the rear surface side of the piezoelectric body. Thus, occurrence of deterioration of a diagnostic image can be suppressed.

It was possible to obtain backing materials having a high attenuation and high heat conduction as exhibited by backing materials 13 to 16 by changing the matrix resin to be used from a liquid epoxy resin to a powder epoxy resin. Backing materials 13 to 16 can efficiently radiate heat generated in the piezoelectric element because of their high heat conductivity, and thus can suppress overheat of the acoustic lens in contact with the subject. Additionally, due to a large attenuation of ultrasound, reflection of ultrasound transmitted to the rear surface side can be suppressed, and thus, tomographic images of high image quality can be obtained.

Figure 3A:
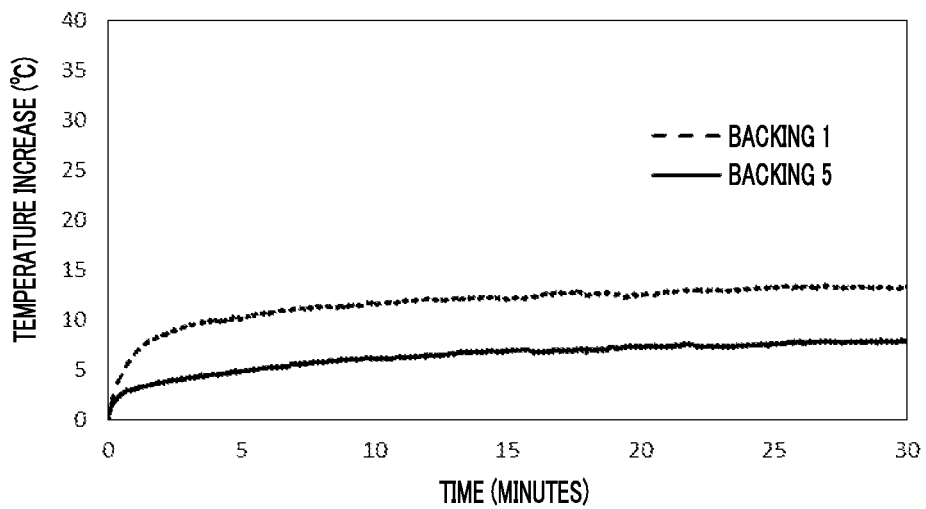
FIG. 3A is a graph showing the heat radiation effect of the ultrasound probe according to the embodiment of the present invention.
Figure 3B:
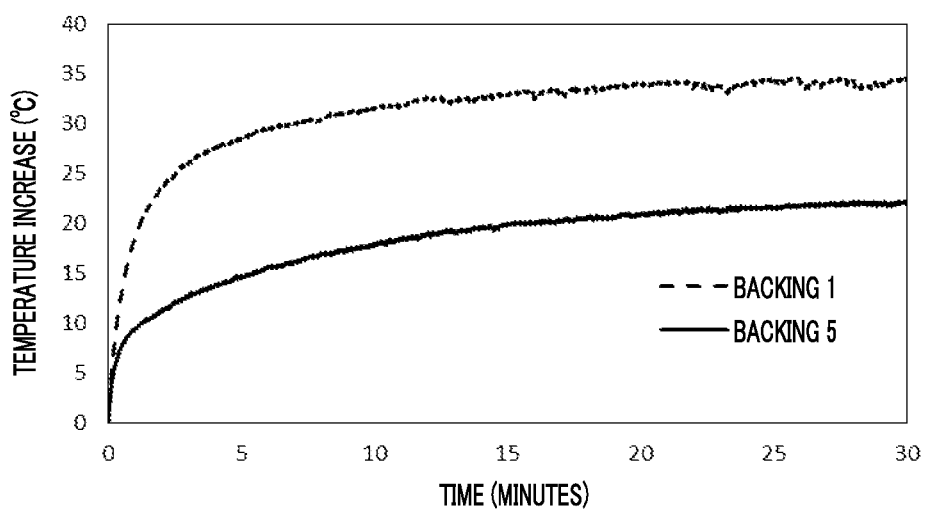
FIG. 3B is a graph showing the heat radiation effect of the ultrasound probe according to the embodiment of the present invention.

FIG. 3A is a graph showing the heat radiation effect of backing materials 1 and 5 when the input voltage is set to 60 Vpp. FIG. 3B is a graph showing the heat radiation effect of backing materials 1 and 5 when the input voltage is set to 100 Vpp. The measurements of the temperature increase in the acoustic lens shown in FIG. 3A and FIG. 3B are values obtained by measurement using a thermography camera "FLIR C2" (manufactured by FLIR Systems, Inc.).

From FIG. 3, it can be seen that use of the backing material of the present invention reduced heat generation of the acoustic lens even in the case where a high voltage was applied. It is conceived that this is because use of composite particles as the heat conductive particles can reduce the heat conductive particles to be used.

(Processability of Backing Materials)

The moldability, durability, and dicing property of backing materials 1 to 16 were evaluated.

(Moldability)

Evaluation was performed by using backing materials 1, 3 to 11, and 13 molded to a diameter of 50 mm and a height of 20 mm by the method described above.

(Evaluation Method)

Backing materials 1 to 16 cut by a wire saw "CS-203" (manufactured by Musashino Denshi Inc.) and further polished to a thickness of 10 mm by a precision polisher "MA-200" (manufactured by Musashino Denshi Inc.) were observed with an optical microscope or visually to check air bubbles and a degree of cracking. A and B were accepted.

(Evaluation Criteria)

A: No air bubbles and cracks occur, and them is no particle bias.

B: Less than 3 air bubbles and cracks occur, and there is no particle bias.

C: Less than 6 air bubbles and cracks occur, and a bias of a portion of particles occurs.

D: 6 or more air bubbles and cracks occur, and a bias of particles occurs.

(Durability)

Backing materials 1 to 16 prepared by the method mentioned above were each cut into a size of 30 mm×30 mm×1 mm. This was used as a test piece and immersed in oleic acid at 25° C. to observe the swelling condition. A and B were accepted.

(Evaluation Criteria)

A: The degree of swelling is less than 3%.

B: The degree of swelling is 3% or more and less than 5%.

C: The degree of swelling is 5% or more and less than 10%.

D: The degree of swelling is 10% or more.

(Dicing Property)

A matching layer, a piezoelectric material, a flexible printed circuit (FPC), a backing material, and the like were bonded in a TD shape, and this bonded product was diced by a 20-μm blade with a 50-μm pitch and at an aspect ratio of about 6 (total film thickness: 300 μm). The number of such products prepared was 500. Among these, the number of products having a capacity changed from the theoretical value was checked. C or higher were accepted.

(Evaluation Criteria)

A: Less than 3/500

B: Less than 10/500

C: Less than 200/500

D: 200/500 or more

The moldability, durability, and dicing property of backing materials 1 to 13 are shown in Table 4.

TABLE 4

| Backing | Processability | | |
|---|---|---|---|
| | Moldability | Durability | Dicing property |
| 1 | A | C | A |
| 2 | D | D | C |
| 3 | C | B | C |
| 4 | A | A | B |
| 5 | B | B | A |
| 6 | B | B | B |
| 7 | B | B | B |
| 8 | B | B | A |
| 9 | B | B | A |
| 10 | B | B | A |
| 11 | A | B | A |
| 12 | B | B | B |
| 13 | A | A | A |
| 14 | A | A | A |
| 15 | A | A | A |
| 16 | A | A | A |

It was possible to obtain a backing material excellent in processability by setting the content of the heat conductive particles to less than 30 vol % based on the total mass of the components constituting the backing material. It was possible to obtain a backing material excellent in moldability, durability, and dicing property, particularly by using a powder epoxy resin as the matrix resin. It is conceived that this is because the arrangement of the heat conductive particles can be controlled by using a powder epoxy resin as the matrix resin.

INDUSTRIAL APPLICABILITY

The ultrasound probe of the present invention has a high heat radiation property due to the backing material and provides less deterioration of image quality because of enhanced heat conduction of the backing material, enabling imaging at a higher voltage. The probe is useful as an ultrasound probe of an ultrasound apparatus having higher sensitivity.

Although embodiments of the present invention have been described and illustrated in detail, the disclosed embodiments are made for purposes of illustration and example only and not limitation. The scope of the present invention should be interpreted by terms of the appended claims

What is claimed is:

1. An ultrasound probe, comprising:
a piezoelectric element; and
a backing material disposed on one direction side with respect to the piezoelectric element, the backing material containing heat conductive particles and non-heat conductive particles dispersed in a base material, wherein
a ratio of a volume of the heat conductive particles based on a total volume of the non-heat conductive particles is in the range 1/10 to 1/1,
the heat conductive particles have a heat conductivity of 60 W/mK to 5,000 W/mK,
the average particle size of the heat conductive particles is in the range including 10 μm to 150 μm,
the backing material has a heat conductivity of 2.0 W/mk or more, and
a content of the heat conductive particles is less than 30 vol % based on a total volume of the backing material.

2. The ultrasound probe according to claim 1, wherein the heat conductive particles are part of composite particles with an average particle size in the range of 100 μm to 350 μm.

3. The ultrasound probe according to claim 2, wherein the composite particles include the heat conductive particles and an elastomer.

4. The ultrasound probe according to claim 3, wherein the elastomer has a tensile breaking elongation of 160% or less.

5. The ultrasound probe according to claim 1, wherein the non-heat conductive particles are composite particles.

6. The ultrasound probe according to claim 1, wherein the ratio of the volume of the heat conductive particles based on the total volume of the non-heat conductive particles is 1/5 or more and 1/2 or less.

7. The ultrasound probe according to claim 1, wherein the base material further contains a matrix resin as a powder.

8. The ultrasound probe according to claim 7, wherein the matrix resin is a thermosetting resin having a glass transition temperature (Tg) of 100° C. or more and 200° C. or less.

9. An ultrasound diagnostic apparatus, comprising the ultrasound probe according to claim 1.

10. The ultrasound probe according to claim 1, wherein a content of the non-heat conductive particles in the backing material is in the range of 30 to 45 vol %.

11. The ultrasound probe according to claim 1, wherein the content of the heat conductive particles is 6 vol % or more and 15 vol % or less based on the total volume of the backing material.

12. A method for producing a backing material for an ultrasound probe, the method comprising:
mixing a matrix resin, a heat conductive resin, and non-heat conductive particles to prepare a mixture, the heat conductive resin including heat conductive particles with a heat conductivity of 60 W/mK to 5,000 W/mK, and the average particle size of the heat conductive particles being in the range including 10 μm to 150 μm, and
molding the mixture, wherein
a ratio, in the mixture, of a volume of the heat conductive particles based on a total volume of the non-heat conductive particles is in the range 1/10 to 1/1,
the mixture contains less than 30 vol % of the heat conductive particles based on a total volume of the mixture, and
the mixture has a heat conductivity of 2.0 W/mk or more.

* * * * *